US006780417B2

(12) United States Patent
Kaslow et al.

(10) Patent No.: US 6,780,417 B2
(45) Date of Patent: Aug. 24, 2004

(54) TRANSMISSION BLOCKING IMMUNOGEN FROM MALARIA

(75) Inventors: David C. Kaslow, Kensington, MD (US); Stuart Isaacs, Kensington, MD (US); Bernard Moss, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/400,421

(22) Filed: Mar. 2, 1995

(65) Prior Publication Data

US 2003/0049278 A1 Mar. 13, 2003

Related U.S. Application Data

(63) Continuation of application No. 08/110,457, filed on Aug. 23, 1993, now abandoned, which is a continuation of application No. 07/908,765, filed on Jul. 1, 1992, now abandoned, which is a continuation of application No. 07/658,845, filed on Feb. 22, 1991, now abandoned.

(51) Int. Cl.[7] ...................... A61K 39/015; C12N 15/30
(52) U.S. Cl. ............................... 424/199.1; 424/191.1; 424/268.1; 424/272.1; 435/69.3; 435/320.1
(58) Field of Search .......................... 424/268.1, 272.1, 424/191.1; 435/69.1, 199.1, 235.1, 69.3, 320.1

(56) References Cited

U.S. PATENT DOCUMENTS

| | | | |
|---|---|---|---|
| 4,546,082 A | 10/1985 | Kurjan et al. | 435/172.3 |
| 4,707,445 A | 11/1987 | McCutchan et al. | 435/91 |
| 4,735,799 A | 4/1988 | Patarroyo | 424/88 |
| 4,769,330 A | 9/1988 | Paoletti et al. | 435/172.3 |
| 4,826,957 A | 5/1989 | Nussenzweig et al. | 530/350 |
| 5,217,898 A | 6/1993 | Kaslow et al. | 435/255 |
| 5,853,739 A | * 12/1998 | Kaslow et al. | 424/268.1 |

FOREIGN PATENT DOCUMENTS

WO    WO89/10936    * 11/1989    ............ C07K/7/10

OTHER PUBLICATIONS

Tine et al., Sep. 1996. NYVAC–Pf7: a Poxvirus–Vectored, Multiantigen, Multistage, Vaccine Candidate for *Plasmodium falciparum* Malaria. Infection and Immunity 64(9): 3833–3844, 1996.*
Smith et al Parasitology 91: S109–S117, 1986.*
Mitchell Parasitology 98:529–547, An Update on Candidate Malaria Vaccines.*
Pye et al Infect & Immunity 59: 2403–2411, 1991 Failure of Recombinant Vaccinia Viruses Expressing: Plasmodun Falciparum Antigers to Protect Saimiri Monkey Against Malarial.*

Kaslow Immunology Letters 25:8386 1990.*
Kaslow et al Nature 333:74–76, 1988.*
Kaslow Abstract. World/Health Organization Meeting in Geneva, Oct. 1990.*
Kaslow Abstract Presented a Molecular Parasitology Sep. 9–12, 1990.*
Butcher, Parasitology 98:315–327.*
Kaslow, Vaccine Research Toward a Transmission Blocking Vaccine for Malaria 2:197–205, 1993.*
Carter et al, The Journal of Exp. Med 169:135–147, 1989.*
S. Vijaya et al., (1988) "Transport to the Cell Surface of a Peptide Sequence Attached to the Truncated C Terminus of an N–Terminally Anchored Integral Membrane Protein", *Molecular And Cellular Biology*, vol. 8 No. 4:1709–1714.
Langford et al., (1986) "Anchoring a Secreted Plasmodium Antigen on the Surface of Recombinant Vaccinia Virus–Infected Cells Increases Its Immunogenicity", *Molecular And Cellular Biology*, vol. 6 No. 9:3191–3199.
Kaslow et al., (1988) "A Vaccine Candidate from the Sexual Stage of Human Malaria that Contains EGF–like Domains", *Nature*, vol. 333:74–76.
A.M. Lew et al., (1988) "Comparison of Antibody Avidity and Titre Elicited by Peptide as a Protein Conjugate or as Expressed in Vaccinia", *Immunology*, vol. 65:311–314.
Vermeulen et al., (1985) "Sequential Expression of Antigens on Sexual Stages of *Plasmodium Falciparum* Accessible to Transmission–Blocking Antibodies in the Mosquito", *J. Exp. Med.*, vol. 162:1460–1476.
Ballo et al., (1985) "Immunogenicity of Synthetic Peptides from Circumsporozoite Protein of *Plasmodium falciparum*", *Science*, vol. 228:996–998.
Kaslow et al., (1991) "Induction of *Plasmodium falciparum* Transmission–Blocking Antibodies by Recombinant Vaccinia Virus", *Science*, vol. 252:1310–1313.
Kaslow, David C., (1990) "Immunogenicity of *Plasmodium falciparum* sexual stage antigens: implications for the design of a transmission blocking vaccine", *Immunology Letters*, vol. 25:83–86.

(List continued on next page.)

*Primary Examiner*—Christopher L. Chin
*Assistant Examiner*—James L. Grun
(74) *Attorney, Agent, or Firm*—Townsend and Townsend and Crew LLP

(57) ABSTRACT

The present invention relates to transmission blocking vaccines against malaria. Vaccines of the present invention contain a recombinant virus encoding all, or a unique portion, of the 25 kDa sexual stage surface protein of *Plasmodium falciparum*, Pfs25, or the Pfs25 protein purified from host cells infected with the above-described recombinant virus. Mice inoculated with the recombinant virus developed antibodies with transmission blocking activity. The present invention also relates to recombinant viruses used in the vaccines of the present invention, host cells infected with the recombinant viruses of the present invention and methods of preventing or treating malarial infections using the vaccines of the present invention.

4 Claims, 1 Drawing Sheet

OTHER PUBLICATIONS

Kaslow, David C., (1993) "Toward a Transmission–Blocking Vaccine for Malaria", *Vaccine Research*, vol. 2 No. 3:197–205.

Butcher, G.A., (1989) "Mechanisms of immunity to malaria and the possibilities of a blood–stage vaccine: a critical appraisal", *Parisitology*, vol. 98:315–327.

Pye et al., (1991) "Failure of Recombinant Vaccinia Viruses Expressing *Plasmodium falciparum* Antigens To Protect *Saimiri* Monkeys against Malaria", *Infection And Immunity*, vol. 59 No. 7:2403–2411.

Mitchell, G.H., (1989) "An update on candidate malaria vaccines", *Parasitology*, vol. 98:S29–S47.

Kaslow, David C., "Cloning and expression of *P. falciparum* sexual stage antigens", Presented at Molecular Parasitology, Session 5, Sep. 9–12, 1990.

Kaslow et al., Abstract 126 from the World Health Organization Meeting, Oct. 1990.

Gibson et al., Abstract 219 from the 38th Annual Meeting of the American Society of Tropical Medicine and Hygiene, Dec. 1989.

Kaslow et al., (1993) "Safety, Immunogenicity, and In Vitro Efficacy of a Muramyl Tripeptide–Based Malaria Transmission–Blocking Vaccine in an *Aotus nancymai* Monkey Model", *Vaccine Research*, vol. 2 No. 2:95–103.

Rawlings and Kaslow, (1992) "Adjuvant–dependent Immune Response to Malarial Transmission–blocking Vaccine Candidate Antigens", *J. Exp. Med.*, vol. 1761483–1487.

Brake et al., (1984) "a–Factor–directed synthesis and secretion of mature foreign proteins in *Saccharomyces cerevisiae*", *Proc. Natl Acad. Sci. USA*, vol. 81:4642–4646.

Abrignani et al., (1990) "Priming of CD4+T cells specific for conserved regions of human immunodeficiency virus glycoprotein gp120 in humans immunized with a recombinant envelope protein", *Proc. Natl Acad. Sci. USA*, vol. 87:6136–6140.

Miller et al., (1986) "Research Toward Malaria Vaccines", *Science*, vol. 234:1349–1356.

Barr et a., (1988) "Expression and Processing of Biologically Active Fibroblast Growth Factors in the Yeast *Saccharomyces cerevisiae*", *Journal of Biological Chemistry*, vol. 263, No. 31:16471–16478.

Cox, Francis (1991) "Malaria vaccines—progress and problems", *Tibtech*, vol. 9:389–394.

Carter et al., (1989) "Restricted or Absent Immune Responses in Human Populations to *Plasmodium Falciparum* Gamete Antigens that are Targets of Malaria Transmission–Blocking Antibodies", *Journal of Experimental Medicine*, vol. 169:135–147.

Dame et al., (1984) "Structure of the Gene Encoding the Immunodominant Surface Antigen on the Sporozoite of the Human Malaria Parasite *Plasmodium falciparum*", *Science*, vol. 225:593–598.

* cited by examiner

TRANSMISSION BLOCKING IMMUNOGEN FROM MALARIA

The present application is a continuation of U.S. patent application Ser. No. 08/110,457, filed Aug. 23, 1993, now abandoned, which is a continuation of U.S. Ser. No. 07/908,765, filed Jul. 1, 1992, now abandoned, which is a continuation of U.S. Ser. No. 07/658,845, filed Feb. 22, 1991, now abandoned. Each of the aforementioned applications is explicitly incorporated herein by reference in their entirety and for all purposes.

BACKGROUND OF THE INVENTION

1. Field of the Invention

The present invention relates to transmission blocking vaccines against malaria and methods of preventing the transmission of the disease. The invention further relates to recombinant virus encoding a *Plasmodium falciparum* sexual stage surface protein and to host cells infected therewith.

2. Background Information

Malaria continues to exact a heavy toll from mankind. The major cause of malaria in humans is the parasite *Plasmodium falciparum*. Approximately 25 percent of all deaths of children in rural Africa between the ages of one to four years are caused by malaria.

The value of various vaccines to combat malaria is appreciated through an understanding of the life cycle of the parasite. Infection in man begins when young malarial parasites or "sporozoites" are injected into the bloodstream of a human by the mosquito. After injection the parasite localizes in liver cells. After approximately one week the parasites or "merozoites" are released into the bloodstream. The entry of the parasites into the bloodstream begins the "erythrocytic" phase. Each parasite enters the red blood cell in order to grow and develop. When the merozoite matures in the red blood cell, it is known as a trophozoite and schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or "macrogametocyte" and the male parasite or "microgametocyte." These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete into a macrogamete. The fertilized parasite is known as a zygote that develops into an "ookinete." The ookinete penetrates the midgut wall of the mosquito and transforms into the oocyst within which many small sporozoites form. When the oocyst ruptures the sporozoites migrate to the salivary gland of the mosquito via the hemolymph. Once in the saliva of the mosquito, the parasite can be injected into a host.

Malaria vaccines are being developed against different stages in the parasite's life-cycle which includes the sporozoite, asexual erythrocyte, and sexual stage. Each development increases the opportunity to control malaria in the many diverse settings within which the disease occurs. Sporozoite vaccines would prevent mosquito-induced infections. First generation vaccines of this type have been tested in humans. Asexual erythrocytic stage vaccines would be useful in reducing the severity of the disease. Multiple candidate antigens have been cloned and tested in animals and in humans.

One type of vaccine being investigated to slow or reverse the worsening epidemic of malaria is a transmission blocking vaccine [Miller et al., *Science* 234:1349 (1988)]. Transmission of *Plasmodium falciparum* from host to mosquito vector can be blocked by monoclonal antibodies against a 25 kDa sexual stage surface protein, Pfs25, expressed on zygotes and ookinetes [Vermeulen et al., *J. Exp. Med.* 162:1460 (1985)]. The gene encoding Pfs25 has been cloned [Kaslow et al., *Nature* 333:74 (1988)], and the deduced amino acid sequence revealed a striking feature, the presence of four tandem epidermal growth factor (EGF)-like domains. EGF-like domains are cysteine rich and depend on proper disulfide bond formation for structural integrity [Savage et al., *J. Biol. Chem.* 247:7612 (1972)]. It is not surprising, therefore, that of the monoclonal antibodies known to block transmission, none recognize the reduced Pfs25 antigen [Vermeulen et al., *J. Exp. Med.* 162:1460 (1985) and Carter et al., *Prog. Allergy* 41:193 (1988)], suggesting that for at least some of the blocking epitopes, disulfide bonds are involved in creating proper conformation.

A subunit vaccine for controlling endemic malaria in developing countries needs to induce high, long-lasting antibody titers, and be produced in large amounts, at the lowest possible cost. Bacteria or yeast provide a simple means of recombinant protein expression that is inexpensive, if the recombinant products are easily purified and immunologically effective. Live attenuated viruses, such as vaccinia or adenovirus, are an attractive alternative because they too are inexpensive to produce, and in addition, are easily transported and administered. Furthermore, as the antigen is produced in the mammalian host's cells, proper folding and post-translational modification are more likely to occur than in prokaryotic expression systems.

SUMMARY OF THE INVENTION

Accordingly, it is one object of the present invention to provide a transmission blocking vaccine for humans against malaria which is inexpensive to produce and easily transported and administered.

It is a further object of the present invention to provide a means of producing transmission blocking antibodies against malaria in humans.

Various other objects and advantages of the present invention will become apparent from the following description of the invention together with the figures.

In one embodiment, the present invention relates to a recombinant virus encoding a 25 kDa sexual stage surface protein, Pfs25 of *Plasmodium falciparum* or encoding at least 6 amino acids of Pfs25 and to host cells infected therewith which express the Pfs25 protein on their surface.

In another embodiment, the present invention relates to a transmission blocking vaccine against malaria. The vaccine can comprising a recombinant virus encoding Pfs25 of *Plasmodium falciparum*, a recombinant virus encoding at least 6 amino acids of Pfs25 or Pfs25 purified from a recombinant system such as host cells of the present invention, in an amount sufficient to induce immunization against malaria, and a pharmaceutically acceptable carrier.

In a further embodiment, the present invention relates to a method of preventing transmission of malarial infection.

The method comprising administering to a patient a recombinant virus of the present invention or Pfs25 protein purified from host cells of the present invention, in an amount sufficient to induce transmission blocking activity.

DETAILED DESCRIPTION OF THE INVENTION

Figure 1:
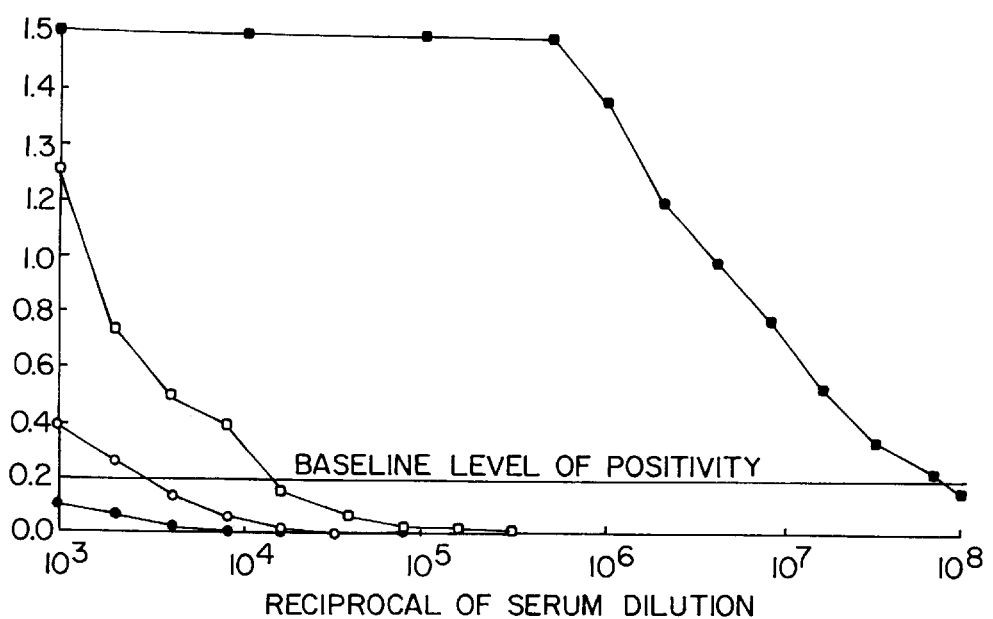
FIG. 1 demonstrates that following tertiary inoculation (open squares) by tail scratch with $10^7$ pfu of vSIDK, ELISA titer of antibodies to Pfs25 increased five-fold over the primary immune response (open circles). Control antibody (closed circle) was below baseline positivity at a dilution of $1:10^3$, while a $1:10^8$ dilution of a 200 µg/ml solution of purified MAb 1D2 (closed squares) was required to reach baseline positivity.

The present invention relates to transmission blocking vaccines against malaria. The present invention is based on studies that involved the preparation of recombinant vaccinia viruses containing the gene encoding Pfs25 and the use of such viruses as a live attenuated vector for the expression of Pfs25 in mammalian cells in vitro and for inoculation of mice to determine immunogenicity and efficacy as a vaccine. From these studies, it was determined that Pfs25 elicits the production of transmission blocking antibodies.

Accordingly, the present invention relates to recombinant attenuated viruses encoding the 25 kDa sexual stage surface protein of *Plasmodium falciparum*, designated Pfs25. The present invention also relates to recombinant attenuated viruses encoding a unique portion of Pfs25, wherein a unique portion consists of at least 5 or 6 amino acids, wherein the unique portions are advantageously antigenic. The viruses are attenuated using methods known in the art, for example, the method described in Bueller et al., *Nature* 317:813 (1985).

Suitable viruses for use in the present invention include, but are not limited to, pox viruses, such as, for example, canarypox and cowpox viruses, and vaccinia viruses, alpha viruses, adenoviruses, and other animal viruses. The recombinant viruses can be produced methods well known in the art, for example, using homologous recombination or ligating two plasmids together. A recombinant canarypox or coxpox virus can be made, for example, by inserting the gene encoding Pfs25 into a plasmid so that it is flanked with viral sequences on both sides. The gene is then inserted into the virus genome throught homologous recombination.

A recombinant adenovirus virus can be produced, of example, by ligating together two plasmid each containing 50% of the viral sequence and the DNA sequence encoding Pfs25. Recombinant RNA viruses such as the alpha virus can made via a cDNA intermediate using methods known in the art.

The recombinant virus of the present invention can be used to induce anti-Pfs25 antibodies in mammals, such as mice or humans. In addition, the recombinant virus can be used to produce Pfs25 protein by infecting host cells which in turn express Pfs25.

The present invention also relates to host cells infected with the recombinant virus of the present invention. The host cells of the present invention are preferably mammalian, such as BSC-1 cells. Host cells infected with the recombinant virus expressed the Pfs25 protein on their cells surface. In addition, membrane extracts of the infected cells induced transmission blocking antibodies when used to inoculate or boost previously inoculated mammals.

The present invention further relates to vaccines against malaria. In particular, the present invention relates to a transmission blocking vaccine. A transmission blocking vaccine prevents the transmission of *Plasmodium falciparum* from host to mosquito vector. While it was previously known that monoclonal antibodies against Pfs25 block the transmission of the parasite from the host to the mosquito, the present inventors have discovered that the inoculation of the recombinant virus elicits the production of polyclonal transmission blocking antibodies which provide greater transmission blocking activity than the monoclonal antibodies to Pfs25.

One transmission blocking vaccine of the present invention comprises the attenuated recombinant virus of the present invention encoding all, or a unique portion, of Pfs25 of *Plasmodium falciparum* and a pharmaceutically acceptable carrier. The vaccine may also include adjuvant. The recombinant virus is present in the vaccine in an amount sufficient to induce immunization against malaria. The vaccine can be administered via intradermal, subcutaneous, intramuscular, nasopharyngeal or respiratory routes, for example, inhalation.

Another transmission blocking vaccine of the present invention comprises Pfs25 or a unique peptide thereof, purified from host cells infected with the recombinant virus, and a pharmaceutically acceptable carrier. The protein is purified using standard purification techniques known in the art. This embodiment of the vaccine is particularly useful for booster inoculations. Mice inoculated with the recombinant virus have a relatively low antibody titer, however, when these mice are given subsequent booster inoculations of purified host cell membrane extracts their antibody titers increase as does the transmission blocking activity of the antibodies.

The transmission blocking vaccines of the present invention can also include other malarial antigens. For example, the transmission blocking vaccine of the present invention include antigens generating protective malarial antibodies.

The present invention also relates to methods of preventing transmission of malarial infections. Methods of the present invention comprise administering to a patient a vaccine of the present invention in an amount sufficient to induce transmission blocking activity. The treatment consists of a single administration or a series of administrations. Furthermore, in a series of administrations, it is not necessary to give same vaccine at each administration. For example, a patient can initially be given a vaccine containing a recombinant virus and then given booster inoculations with a vaccine containing the Pfs25 protein made in any number of recombinant expression systems, or given booster inoculations with another live attenuated recombinant virus expressing Pfs25 or a unique portion thereof. Preferably, a patient is initially given the virus containing vaccine and if necessary, given booster inoculations of either the virus containing vaccine or the protein containing vaccine.

When given as a series administrations, inoculations subsequent to the initial administration are given to boost the immune response and may be referred to as booster inoculations. The treatment given will vary in the number of inoculations and the vaccine used depending on several factors, such as the patient's conditions and the route of administration. These factors are easily assessed by the physician and an appropriate treatment determined therefrom.

The following examples are given to further illustrate the present invention without being deemed limitative thereof.

EXAMPLES

The gene coding Pfs25 (SEQ ID NO: 1) was cloned as previously described [Kaslow et al., Nature 333:74 (1988) and U.S. patent application Ser. No. 07/188,918 filed May 2, 1988, both are hereby incorporated in their entirety (SEQ ID NOS: 1: and 2)]. The full length gene was then inserted into the vaccinia virus (strain WR) genome by homologous recombination using a transfer vector, pTKgpt-OFIS [Falkner et al., J. Virology 63:1849 (1988)]. The resulting recombinant virus, vSIDK, was thymidine kinase deficient, mycophenolic acid resistant, and expressed Pfs25 (SEQ ID NO: 1) under the control of the vaccine P11 late promoter. The recombinant virus, vSIDK, was isolated and used to infect mammalian BSC-1 cells [Falkner et al., J. Virology 63:1849 (1988)].

Nucleotide (SEQ ID NO:1) and predicted amino acid (SEQ ID NO:2) sequence of Psf25:

examined with normal mouse sera. The reaction with MAb 1C7 was stronger 48 hours after infection than at 24 hours.

To determine antibody titers to rPfs25 in mice inoculated with vSIDK, an ELISA was developed using extracts of vSIDK infected cell as the capture antigen. The optimal concentrations of capture antigen and a reliable means of determining the portion of the signal specific for anti-Pfs25 antibodies in immune sera were determined in pilot studies [Quakyi, I. A., Trop. Med. Para. 42:325 (1980)].

Briefly, HeLa cells were infected at an MOI of 1 to 2 with either the vSIDK or the WR strain of vaccinia virus. After 48 hours the cells were harvested by low speed centrifugation and the cell pellet resuspended in two and half volumes of swelling buffer (10 mM Tris, pH 9.0). The cells were disrupted by three cycles of freeze-thaw in ethanol-dry ice, followed by sonication.

```
AATTGTTGTG AAAAGAAAAA AAGAAAAAAA AAAAAAAAAA AAGTGATACC TTATATTTTT

TTATTCTTTT AAAA ATG AAT AAA CTT TAC AGT TTG TTT CTT TTC CTT TTC
            Met Asn Lys Leu Tyr Ser Leu Phe Leu Phe Leu Phe

ATT CAA CTT AGC ATA AAA TAT AAT AAT CGC AAA GTT ACC GTG GAT ACT
Ile Gln Leu Ser Ile Lys Tyr Asn Asn Ala Lys Val The Val Asp Thr

GTA TGC AAA AGA GGA TTT TTA ATT CAG ATG TGT GGT CAT TTG GAA TGT
Val Cys Lys Arg Gly Phe Leu Ile Gln Met Ser Gly His Leu Glu Cys

AAA TGT GAA AAT GAT TTG GTG TTA GTA AAT GAA GAA AGA TGT GAA GAA
Lys Cys Glu Asn Asp Leu Val Leu Val Asn Glu Glu Thr Cys Glu Glu

AAA GTT CTG AAA TGT GAC GAA AAG ACT GTA AAT AAA CCA TGT GGA GAT
Lys Val Leu Lys Cus Asp Glu Lys The Val Asn Lys Pro Cys Gly Asp

TTT TCC AAA TGT ATT AAA ATA GAT GGA AAT CCC GTT TCA TAC GCT TGT
Phe Ser Lys Cys Ile Lys Ile Asp Gly Asn Pro Val Ser Tyr Ala Cys

AAA TGT AAT CTT GGA TAT GAT ATG GTA AAT AAT GTT TGT ATA CCA AAT
Lys Cys Asn Leu Gly Tyr Asp Met Val Asn Asn Val Cys Ile Pro Asn

GAA TGT AAG AAT GTA ACT TGT GGT AAC GGT AAA TGT ATA TTA GAT ACA
Glu Cys Lys Asn Val The Cus Gly Asn Gly Lys Cys Ile Leu Asp Thr

AGC AAT CCT GTT AAA ACT GGA CTT TGC TCA TGT AAT ATA GGC AAA GTT
Ser Asn Pro Val Lys Thr Gly Val Cys Ser Cys Asn Ile Gly Lys Val

CCC AAY GYA CAA GAY CAA AAY AAA YGY YCA AAA GAY GGA GAA ACC AAA
Pro Asn Val Gln Asp Gln Asn Lys Cys Ser Lys Asp Gly Glu Thr Lys

TGC TCA TTA AAA TGC TTA AAA GAA AAT GAA ACC TGT AAA GCA GTT GAT
Cys Ser Leu Lys Cys Leu Lys Glu Asn Glu Thr Cys Lys Ala Val Asp

GGA ATT TAT AAA TGT GAT TGT AAA GAT GGA TTT ATA ATA GAT AAT GAA
Gly Ile Tyr Lys Cys Asp Cys Lys Asp Gly Phe Ile Ile Asp Asn Glu

AGC TCT ATA TGT ACT GCT TTT TCA GCA TAT AAT ATT TTA AAT CTA AGC
Ser Ser Ile Cys Thr Ala Phe Ser Ala Tyr Asn Ile Leu Asn Leu Ser

ATT ATG TTT ATA CTA TTT TCA GTA TGC TTT TTT ATA ATG TAAATATTAT
Ile Met Phe Ile Leu Phe Ser Val Cys Phe Phe Ile Met

AACAACATAT ATATATATTT TTAAATGGTA AA
```

Recombinant Pfs25 (rPfs25) expression resulted in proper folding of epitopes for MAbs 1C7, 1D2 and 32F61, all of which recognize reduction sensitive epitopes. Furthermore, in striking contrast to Plasmodium circumsporozoite protein [Langford et al., Mol. Cell. Biol. 6:3191 (1986)], rPfs25 appeared on the surface of infected mammalian cells: in indirect immunofluorescence, MAb 1C7 gave a uniform, strong surface fluorescence reaction with vSIDK infected BSC1 cells; while WR infected cells were completely negative in reaction with MAb 1C7, as were vSIDK infected cells The cell lysate was first fractionated on ice for 2–3 hours by allowing the cellular debris to settle out of suspension. The portion still in suspension was further fractionated, by centrifugation at 5,500×g for 10 minutes at 4° C., into membrane bound (pellet) and soluble fractions (supernatant).

The membrane bound fraction was resuspended in coating buffer (15 mM sodium carbonate, 35 mM sodium bicarbonate, 0.02% w/v sodium azide, pH 9.6) at a final concentration of total protein of 10–20 µg/ml. 100 µl of membrane suspension was added to each well of a polystyrene microtiter plate (Immulon 1, Dynatech Labs, VA) and incubated at 4° C. for 16 hours. The wells were subsequently "blocked" with 1% bovine serum albumin (BSA) in coating buffer.

Test serum or monoclonal antibody was then added to each well at various dilutions and incubated at 37° C. for 90 minutes. After thorough washing with 0.5% Tween-20 in PBS (TPBS), a 1:1000 dilution of goat anti-mouse IgG coupled to alkaline phosphate (Jackson ImmunoResearch Laboratories, PA) was added to each well and incubated at 37° C. for 90 minutes. The cells were thoroughly washed with TPBS, and then substrate added, and incubated at 37° C. for 15 minutes.

Absorbance was read at 405 nm. Each well containing vSIDK membrane extract had a matched well containing WR membrane extract. The amount of extract added to each well was adjusted such that matched wells had identical optical density when mouse anti-WR serum was used as the primary antibody. The signal specific for Pfs25 could, therefore, be determined by subtracting the optical density of the WR membrane extract well from the matched vSIDK membrane extract well. When calculated in this manner, a baseline level of positivity was defined as an optical density of 0.20.

Purified MAb 1D2, a transmission blocking monoclonal antibody similar to MAb 1C7, could be detected on ELISA at a dilution greater than 1:10$^8$ (FIG. 1). A concentration of 200 µg/ml of MAb 1D2, which is the equivalent to a 1:2 dilution in the ELISA (FIG. 1), was required for full transmission blocking activity in membrane feeds (see Table 1 below).

After a single tail scratch inoculation with vSIDK, CAF-1 mice developed antibody titers of 1:3000 by ELISA to Pfs25 (FIG. 1). Sera from these CAF-1 mice failed to block transmission in the absence or presence of complement. When these mice were inoculated two more times with vSIDK virus, antibody titers by ELISA to Pfs25 rose fivefold to 1:16,000 (FIG. 1). At this titer, complete transmission blocking activity in membrane feeds was achieved in the absence of complement (see Table 1 below), even when the immune sera were diluted 1:20.

TABLE 1

| Antisera | Dilution or Concentration | Mean Oocyst # (range) | Infectivity % of control | Mosq. Inf Mosq. Dis |
|---|---|---|---|---|
| Normal Human | 1:2 | 9 (4–20) | 100 | 16/16 |
| anti-WR | 1:2 | 9 (3–23) | 100 | 21/21 |
| MAb 1D2 | 1:2 200 µg/ml | 0.1 (0–1) | 1 | 2/19 |
| MAb 1D2 | 1:4 100 µg/ml | 1 (0–6) | 11 | 5/11 |
| MAb 1D2 | (1:8) 50 µg/ml | 1.4 (0–10) | 16 | 7/11 |
| MAb 1D2 | 1:16 25 µg/ml | 3.5 (0–11) | 39 | 12/25 |
| CAF-1 A | neat | 0 (0) | 0 | 0/26 |
| CAF-1 A | 1:2 | 0 (0) | 0 | 0/16 |
| CAF-1 B | neat | 0 (0) | 0 | 0/22 |
| CAF-1 B | 1:2 | 0 (0) | 0 | 0/20 |

Table 1. Complete transmission blocking activity after tertiary inoculation of CAF-1 mice with vSIDK. Sera or MAb 1D2 were mixed with *P. falciparum* gametocytes and fed to *A. freeborni* via a membrane feeding apparatus. Seven days after engorgement on the bloodmeal, mosquitos were dissected and their midguts examined for *P. falciparum* oocysts [Quakyi et al., J. Immunol. 139: 4213 (1987)]. Control serum is from a CAF-1 mouse inoculated three times with the WR strain of vaccinia virus.

Previous studies have indicated that high (250 µg/ml) antibody titers to Pfs25 were required for complete transmission blocking activity [Ponnudurai et al., *Trans Roy Soc Trop Med Hyg* 81:491 (1987)]; such titers that might be difficult to achieve and maintain in the field. The data presented herein indicate that much lower titer polyclonal immune sera, achieved by three inoculations with live attenuated virus, have complete transmission blocking activity.

The transmission blocking activity titer of greater than 1:20 in the polyclonal sera was at least ten fold higher than that of MAb 1D2, which was found to have a transmission blocker titer of only 1:2 (see Table 1 above), despite the polyclonal sera having at least a thousand fold lower titer by ELISA than the MAb 1D2 (FIG. 1). Therefore, polyclonal antibody to recombinant Pfs25 appears to be qualitatively, not just quantitatively, better in transmission blocking activity when compared to monoclonal antibodies.

It was previously shown that Ir gene controlled immunoresponsiveness to Pfs25 was nonrestricted in six different strains of H-2 congenic mice immunized with *P. falciparum* zygotes [Good et al. *Science* 242:574 (1988)]. To examine whether there was Ir gene controlled nonresponsiveness to rPfs25 produced by a live attenuated virus and to determine if the ability to induce antibodies that had transmission blocking activity was genetically restricted, the same six congenic mouse strains were inoculated with live vSIDK.

After a single inoculation with vSIDK, all six strains elicited a specific immune response to Pfs25, but failed to block transmission. However, following three inoculations with membrane extracts from vSIDK-infected cells, sera from all mouse strains developed transmission blocking activity (see Table 2 below). These data demonstrate that the capacity to induce transmission blocking antibodies to Pfs25 is not genetically restricted, and suggest that there will be widespread immunological responsiveness in humans.

For inoculation, membrane extracts prepared as described above were treated with psoralen at a final concentration of 5 µg/ml for 10 minutes at room temperature, and the cellular debris allowed to settle at 4° C. for 2 hours. To completely inactivate any live virus, the supernatant was irradiated with long wave (365 nm) ultraviolet at a distance of 10 nm for 4 minutes gentle agitation. A 100 µl aliquot of this preparation was found to have no lytic activity on a monolayer of BSC-1 cells. A one ml aliquot of the psoralen-treated stock (1 mg/ml) was diluted in 5 ml of PBS. Two ml of the diluted stock was added to the Ribi adjuvant system (RIBI ImmunoChem Research, MT), according to the manufacturer's specifications, and 0.2 ml administered into the peritoneum. Mice were boosted on days 21 and 48.

TABLE 2

| Antisera | Concentration or Dilution | Mean Oocyst # (range) | Infectivity % of control | Mosq. Inf Mosq. Dis |
|---|---|---|---|---|
| MAb 1D2 | 200 μg/ml | 0 (0) | 0 | 0/20 |
| WR extract | 1:2 | 4.5 (0–13) | 100 | 14/20 |
| C57B1/10 | 1:2 | 0.1 (0–1) | 2 | 2/20 |
| B10-A (3R) | 1:2 | 0.15 (0–1) | 3 | 3/20 |
| B10-D2 | 1:2 | 0.1 (0–1) | 2 | 2/20 |
| B10-BR | 1:2 | 0.2 (0–2) | 4 | 3/20 |
| B10-S (7R) | 1:2 | 0.05 (0–2) | 1 | 1/20 |
| B10-S (9R) | 1:2 | 0 (0) | 0 | 0/20 |

Table 2. Transmission blocking activity developed in six MHC-disparate congenic mice after three inoculations with membrane extracts of vSIDK-infected cells. Control sera is pooled sera collected from all six congenic mouse strains after three inoculations with membrane extracts from WR strain-infected cells.

Ideally, a transmission blocking vaccine should induce high titer, long-lasting transmission blocking antibodies following a single immunization. Subsequent natural infection would serve to maintain, or boost transmission blocking activity.

In this study, more than a single inoculation with the live, attenuated, recombinant vaccinia virus was necessary to achieve high enough titers of anti-Pfs25 antibodies to block transmission. The low antibody titer observed in mice inoculated only once with recombinant virus may be due, in part, to the reduced replication of virus in mice [Andrew et al., Immunol. Cell. Biol. 67:331 (1989)] infected with recombinant WR strain of vaccinia, in which the thymidine kinase gene has been disrupted.

Subsequent inoculations quantitatively boosted the titer five fold, as measured by ELISA, but also qualitatively changed the antibody, as assayed by transmission blocking activity. The tertiary immunization sera have developed transmission blocking activity that were retained well beyond a five fold dilution. These data suggest that, following boosting, antibodies to new epitopes have been induced, or immunoglobulin class switching or somatic mutation has occurred to produce a more effective transmission blocking antibody. It is expected that Pfs25 is immunogenic in humans, and that a natural infection, following a primary inoculation with recombinant virus, will boost antibodies titers to rPfs25 to levels that will block transmission.

All references cited hereinabove are hereby incorporated by reference.

While the foregoing invention has been described in some detail for purposes of clarity and understanding, it will be appreciated by one skilled in the art from a reading of this disclosure that various changes in form and detail can be made without departing from the scope of the invention.

What is claimed is:

1. An immunogenic composition which primes an immune response in a human capable of inhibiting development of *Plasmodium falciparum* within a mosquito comprising a recombinant vaccinia virus encoding Pfs25 of *Plasmodium falciparum* having amino acid sequence SEQ ID NO: 2 and a pharmaceutically acceptable carrier.

2. The composition according to claim 1 which further comprises an adjuvant.

3. A method of priming an immune response in a human, the method comprising administering to a human patient the composition according to claim 1, thereby priming an immune response in the patient capable of inhibiting the development of *Plasmodium falciparum* within a mosquito.

4. The method according to claim 3, wherein the composition is administered to the patient intradermally, subcutaneously, intramuscularly, nasopharyngeally, or via respiratory routes.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 767 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 75..728
      (D) OTHER INFORMATION: /product= "Pfs25"
           /note= "Plasmodium falciparum clone 3D7
           isolate NF 54 surface protein Pfs25"

(xi) SEQUENCE DESCRIPTION: SEQ ID NO:1:

```
AATTGTTGTG AAAAGAAAAA AACAAAAAAA AAAAAAAAA AACTCATACC TTATATTTTT      60

TTATTCTTTT AAAA ATG AAT AAA CTT TAC AGT TTG TTT CTT TTC CTT TTC     110
              Met Asn Lys Leu Tyr Ser Leu Phe Leu Phe Leu Phe
                1               5                  10

ATT CAA CTT AGC ATA AAA TAT AAT AAT GCG AAA GTT ACC GTG GAT ACT    158
Ile Gln Leu Ser Ile Lys Tyr Asn Asn Ala Lys Val Thr Val Asp Thr
             15                  20                  25

GTA TGC AAA AGA GGA TTT TTA ATT CAG ATG AGT GGT CAT TTG GAA TGT    206
Val Cys Lys Arg Gly Phe Leu Ile Gln Met Ser Gly His Leu Glu Cys
         30                  35                  40

AAA TGT GAA AAT GAT TTG GTG TTA GTA AAT GAA GAA ACA TGT GAA GAA    254
```

-continued

```
Lys Cys Glu Asn Asp Leu Val Leu Val Asn Glu Glu Thr Cys Glu Glu
 45                  50                  55                  60

AAA GTT CTG AAA TGT GAC GAA AAG ACT GTA AAT AAA CCA TGT GGA GAT         302
Lys Val Leu Lys Cys Asp Glu Lys Thr Val Asn Lys Pro Cys Gly Asp
                 65                  70                  75

TTT TCC AAA TGT ATT AAA ATA GAT GGA AAT CCC GTT TCA TAC GCT TGT         350
Phe Ser Lys Cys Ile Lys Ile Asp Gly Asn Pro Val Ser Tyr Ala Cys
             80                  85                  90

AAA TGT AAT CTT GGA TAT GAT ATG GTA AAT AAT GTT TGT ATA CCA AAT         398
Lys Cys Asn Leu Gly Tyr Asp Met Val Asn Asn Val Cys Ile Pro Asn
         95                 100                 105

GAA TGT AAG AAT GTA ACT TGT GGT AAC GGT AAA TGT ATA TTA GAT ACA         446
Glu Cys Lys Asn Val Thr Cys Gly Asn Gly Lys Cys Ile Leu Asp Thr
        110                 115                 120

AGC AAT CCT GTT AAA ACT GGA GTT TGC TCA TGT AAT ATA GGC AAA GTT         494
Ser Asn Pro Val Lys Thr Gly Val Cys Ser Cys Asn Ile Gly Lys Val
125                 130                 135                 140

CCC AAT GTA CAA GAT CAA AAT AAA TGT TCA AAA GAT GGA GAA ACC AAA         542
Pro Asn Val Gln Asp Gln Asn Lys Cys Ser Lys Asp Gly Glu Thr Lys
                145                 150                 155

TGC TCA TTA AAA TGC TTA AAA GAA AAT GAA ACC TGT AAA GCT GTT GAT         590
Cys Ser Leu Lys Cys Leu Lys Glu Asn Glu Thr Cys Lys Ala Val Asp
            160                 165                 170

GGA ATT TAT AAA TGT GAT TGT AAA GAT GGA TTT ATA ATA GAT AAT GAA         638
Gly Ile Tyr Lys Cys Asp Cys Lys Asp Gly Phe Ile Ile Asp Asn Glu
        175                 180                 185

AGC TCT ATA TGT ACT GCT TTT TCA GCA TAT AAT ATT TTA AAT CTA AGC         686
Ser Ser Ile Cys Thr Ala Phe Ser Ala Tyr Asn Ile Leu Asn Leu Ser
190                 195                 200

ATT ATG TTT ATA CTA TTT TCA GTA TGC TTT TTT ATA ATG TAAATATTAT          735
Ile Met Phe Ile Leu Phe Ser Val Cys Phe Phe Ile Met
205                 210                 215

AACAACATAT ATATATATTT TTAAATGGTA AA                                     767
```

(2) INFORMATION FOR SEQ ID NO:2:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Leu Tyr Ser Leu Phe Leu Phe Leu Phe Ile Gln Leu Ser
 1               5                  10                  15

Ile Lys Tyr Asn Asn Ala Lys Val Thr Val Asp Thr Val Cys Lys Arg
                 20                  25                  30

Gly Phe Leu Ile Gln Met Ser Gly His Leu Glu Cys Lys Cys Glu Asn
             35                  40                  45

Asp Leu Val Leu Val Asn Glu Glu Thr Cys Glu Glu Lys Val Leu Lys
         50                  55                  60

Cys Asp Glu Lys Thr Val Asn Lys Pro Cys Gly Asp Phe Ser Lys Cys
 65                  70                  75                  80

Ile Lys Ile Asp Gly Asn Pro Val Ser Tyr Ala Cys Lys Cys Asn Leu
                 85                  90                  95

Gly Tyr Asp Met Val Asn Asn Val Cys Ile Pro Asn Glu Cys Lys Asn
            100                 105                 110

Val Thr Cys Gly Asn Gly Lys Cys Ile Leu Asp Thr Ser Asn Pro Val
```

-continued

```
                115                 120                 125
Lys Thr Gly Val Cys Ser Cys Asn Ile Gly Lys Val Pro Asn Val Gln
    130                 135                 140

Asp Gln Asn Lys Cys Ser Lys Asp Gly Glu Thr Lys Cys Ser Leu Lys
145                 150                 155                 160

Cys Leu Lys Glu Asn Glu Thr Cys Lys Ala Val Asp Gly Ile Tyr Lys
                165                 170                 175

Cys Asp Cys Lys Asp Gly Phe Ile Ile Asp Asn Glu Ser Ser Ile Cys
            180                 185                 190

Thr Ala Phe Ser Ala Tyr Asn Ile Leu Asn Leu Ser Ile Met Phe Ile
        195                 200                 205

Leu Phe Ser Val Cys Phe Phe Ile Met
    210                 215
```